United States Patent [19]

Desanti

[11] Patent Number: 5,123,114
[45] Date of Patent: Jun. 23, 1992

[54] VENTILATED WELDING MASK APPARATUS

[76] Inventor: Michael J. Desanti, 196 Fawn Lake Forest, Hawley, Pa. 18428

[21] Appl. No.: 694,774

[22] Filed: May 2, 1991

[51] Int. Cl.⁵ .............................................. A61F 9/06
[52] U.S. Cl. .............................................. 2/8; 2/171.3
[58] Field of Search ................... 2/8, 9, 424, 171.3, 2/5, 6; 219/147

[56] References Cited

U.S. PATENT DOCUMENTS

| | | | |
|---|---|---|---|
| 3,649,964 | 3/1972 | Schoelz et al. | 2/171.3 X |
| 4,571,741 | 2/1986 | Guillaumot | 2/171.3 |
| 4,694,141 | 9/1987 | Hahn | 2/8 X |

Primary Examiner—Peter Nerbun
Attorney, Agent, or Firm—Leon Gilden

[57] ABSTRACT

A ventilated welding mask is disclosed having a three chamber housing mounted thereon. A blower fan is positioned within a second medial chamber. On the rear wall of the second medial chamber, a nozzle is mounted. A conduit extends from this nozzle to an air flow manifold positioned with the welding mask.

7 Claims, 4 Drawing Sheets

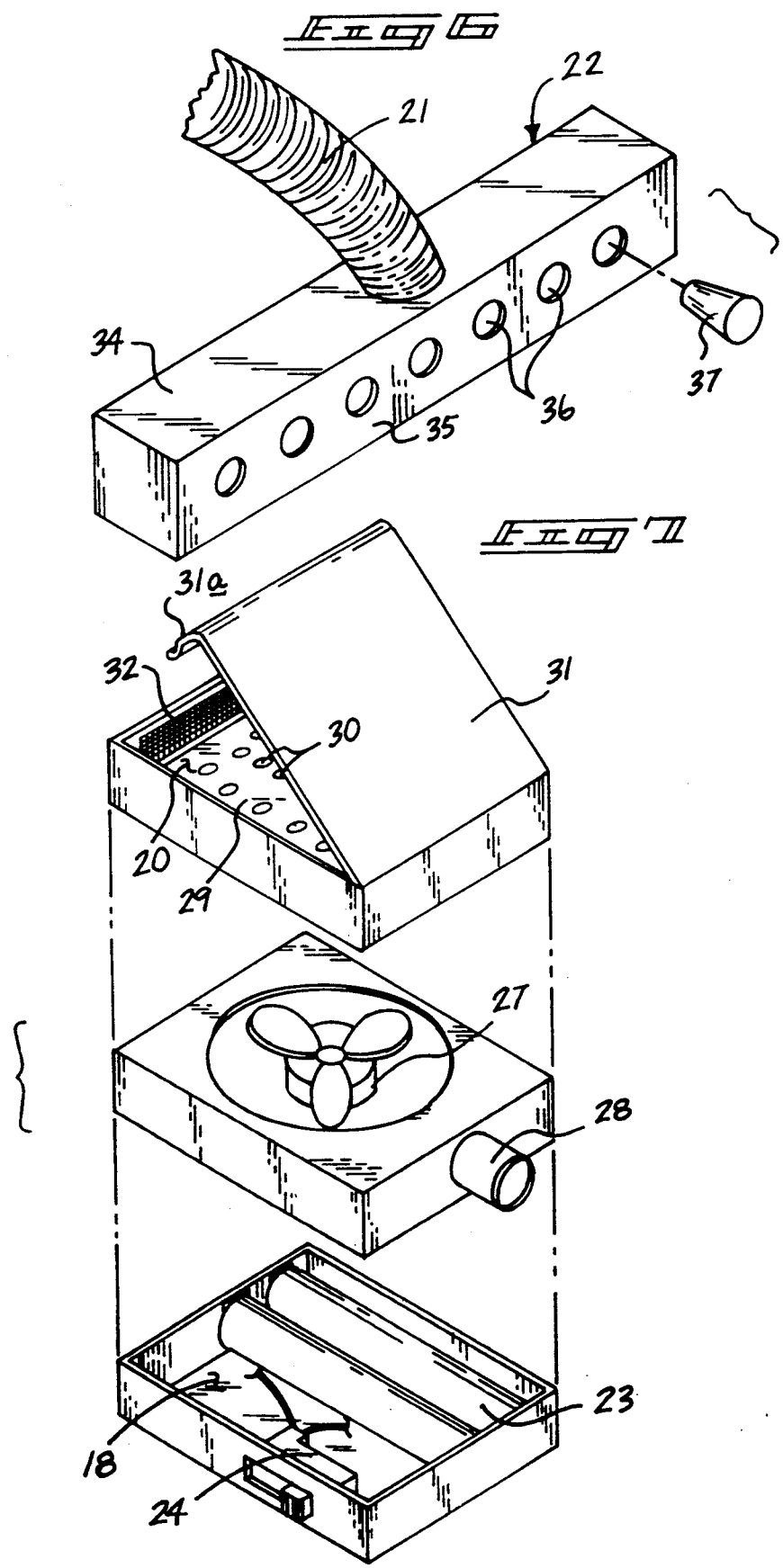

VENTILATED WELDING MASK APPARATUS

BACKGROUND OF THE INVENTION

1. Field of the Invention

The field of invention relates to welding mask apparatus, and more particularly pertains to a new and improved ventilated welding mask apparatus wherein the same directs cooling air to an interior surface of a welding mask to effect cooling and comfort of an individual utilizing the mask.

2. Description of the Prior Art

Various mask apparatus is utilized in the prior art for enhanced ventilation effect to a user thereof.

Such apparatus may be found for example in U.S. Pat. No. 3,657,740 to Cialone wherein a ventilated welding mask utilizes a remotely mounted manifold for directing cooling air through an associated manifold member.

U.S. Pat. No. 3,467,965 to Murphy sets forth a welding hood further utilizing an example of a remote housing for directing cooling medium to the welding mask interior surface.

U.S. Pat. No. 4,890,335 to Crowson sets forth a ventilated welding mask or shield to direct cooling air across a forward and rear surface of the associated window of the welding mask minimizing fogging thereof.

U.S. Pat. No. 3,584,314 to Hobson sets forth a further example of a remotely mounted housing to direct a cooling medium through an associated manifold.

U.S. Pat. No. 3,649,964 to Schoelz, et al. sets forth a ventilated welding mask, wherein the welding mask mounts an integral manifold to the mask, with a duct directed rearwardly and mounted to a rear portion of an associated strap member of the welding mask organization.

As such, it may be appreciated that there continues to be a need for a new and improved ventilated welding mask apparatus as set forth by the instant invention which addresses both the problems of ease of use as well as effectiveness in construction in providing a compact unitary organization to direct both a cooling medium in a compact relationship relative to an interior surface of a welding mask.

SUMMARY OF THE INVENTION

In view of the foregoing disadvantages inherent in the known types of welding mask apparatus now present in the prior art, the present invention provides a ventilated welding mask apparatus wherein the same is arranged to direct a cooled air flow through an interior surface of a welding mask to effect cooling and comfort of an individual's face positioned within the mask. As such, the general purpose of the present invention, which will be described subsequently in greater detail, is to provide a new and improved ventilated welding mask apparatus which has all the advantages of the prior art welding mask apparatus and none of the disadvantages.

To attain this, the present invention provides an apparatus including a helmet mounting a housing thereon. The housing includes a ventilation fan operative through a switch mechanism to direct ventilation air through a manifold along an interior forward wall of the helmet. The organization further includes an upper chamber receiving a predetermined quantity of a cooling medium to direct cooling air through the conduit and the manifold.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved ventilated welding mask apparatus which has all the advantages of the prior art welding mask apparatus and none of the disadvantages.

It is another object of the present invention to provide a new and improved ventilated welding mask apparatus which may be easily and efficiently manufactured and marketed.

It is a further object of the present invention to provide a new and improved ventilated welding mask apparatus which is of a durable and reliable construction.

An even further object of the present invention is to provide a new and improved ventilated welding mask apparatus which is susceptible of a low cost of manufacture with regard to both materials and labor, and which accordingly is then susceptible of low prices of sale to the consuming public, thereby making such ventilated welding mask apparatus economically available to the buying public.

Still yet another object of the present invention is to provide a new and improved ventilated welding mask apparatus which provides in the apparatuses and methods of the prior art some of the advantages thereof, while simultaneously overcoming some of the disadvantages normally associated therewith.

Still another object of the present invention is to provide a new and improved ventilated welding mask apparatus wherein the same is arranged to utilize a cooling medium within the welding mask structure for selective use of a cooling medium to effect chilling of the air directed to the user's face.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an orthographic rear view of the welding mask organization.

FIG. 6 is an orthographic view, taken along the lines 6—6 of FIG. 5 in the direction indicated by the arrows.

FIG. 7 is an isometric exploded illustration of the housing structure mounted to the top wall of the welding mask.

DESCRIPTION OF THE PREFERRED EMBODIMENT

Figure 1:
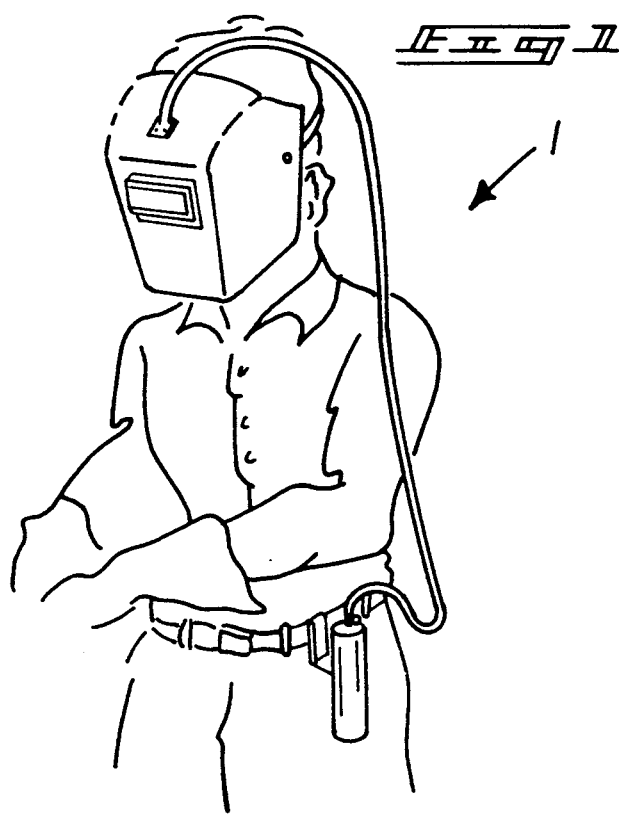
FIG. 1 is an isometric illustration of a prior art welding mask structure.

With reference now to the drawings, and in particular to FIGS. 1 to 7 thereof, a new and improved ventilated welding mask apparatus embodying the principles and concepts of the present invention and generally designated by the reference numeral 10 will be described.

Figure 2:
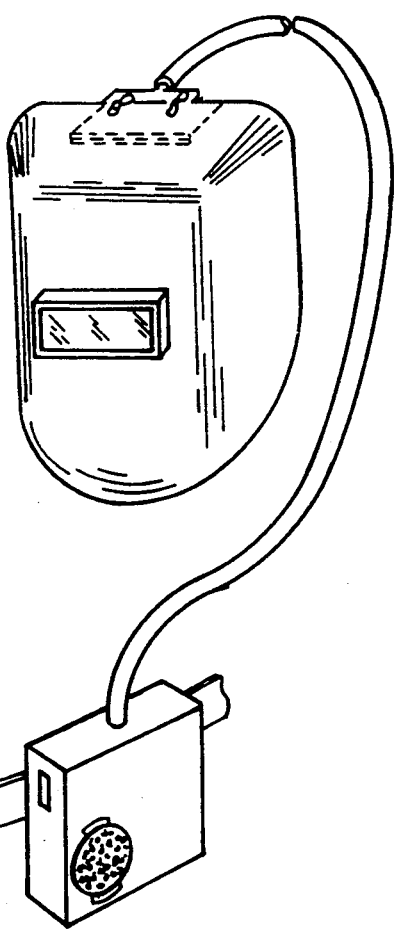
FIG. 2 is an isometric illustration of a further prior art welding mask structure.
Figure 3:
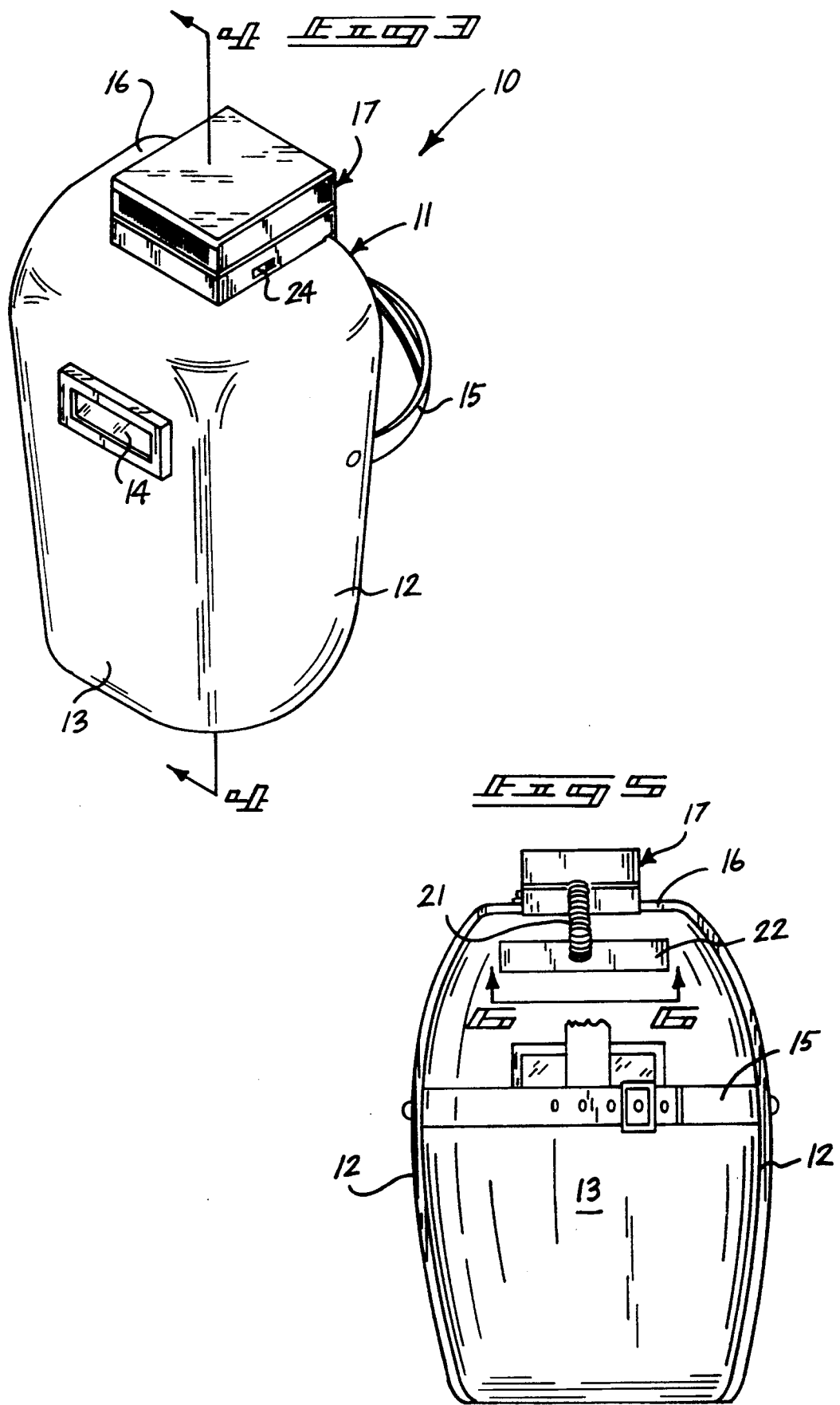
FIG. 3 is an isometric illustration of the instant invention.

FIG. 1 illustrates a prior art welding mask organization 1, as typified in U.S. Pat. No. 3,467,965, wherein a remotely mounted compressor directs a chilled cooling medium into the associated welding mask. FIG. 2 illustrates a further prior art welding mask organization, as indicated and set forth in U.S. Pat. No. 3,657,740, utilizing a remotely mounted fan member utilizing an air conduit to direct ventilation air through a manifold selectively mounted to a top wall of the welding mask structure.

More specifically, the ventilated welding mask apparatus 10 of the instant invention essentially comprises a unitary helmet member 11 formed with spaced side walls 12, a forward wall 13, and a top wall 16. The forward wall 13 includes a viewing window 14 mounted to the forward wall, with the side walls 12 including a securement strap member 15 mounted thereto, with the securement member including a lateral encircling strap, with a top strap mounted diametrically and orthogonally to a top portion of the encircling strap.

Figure 4:
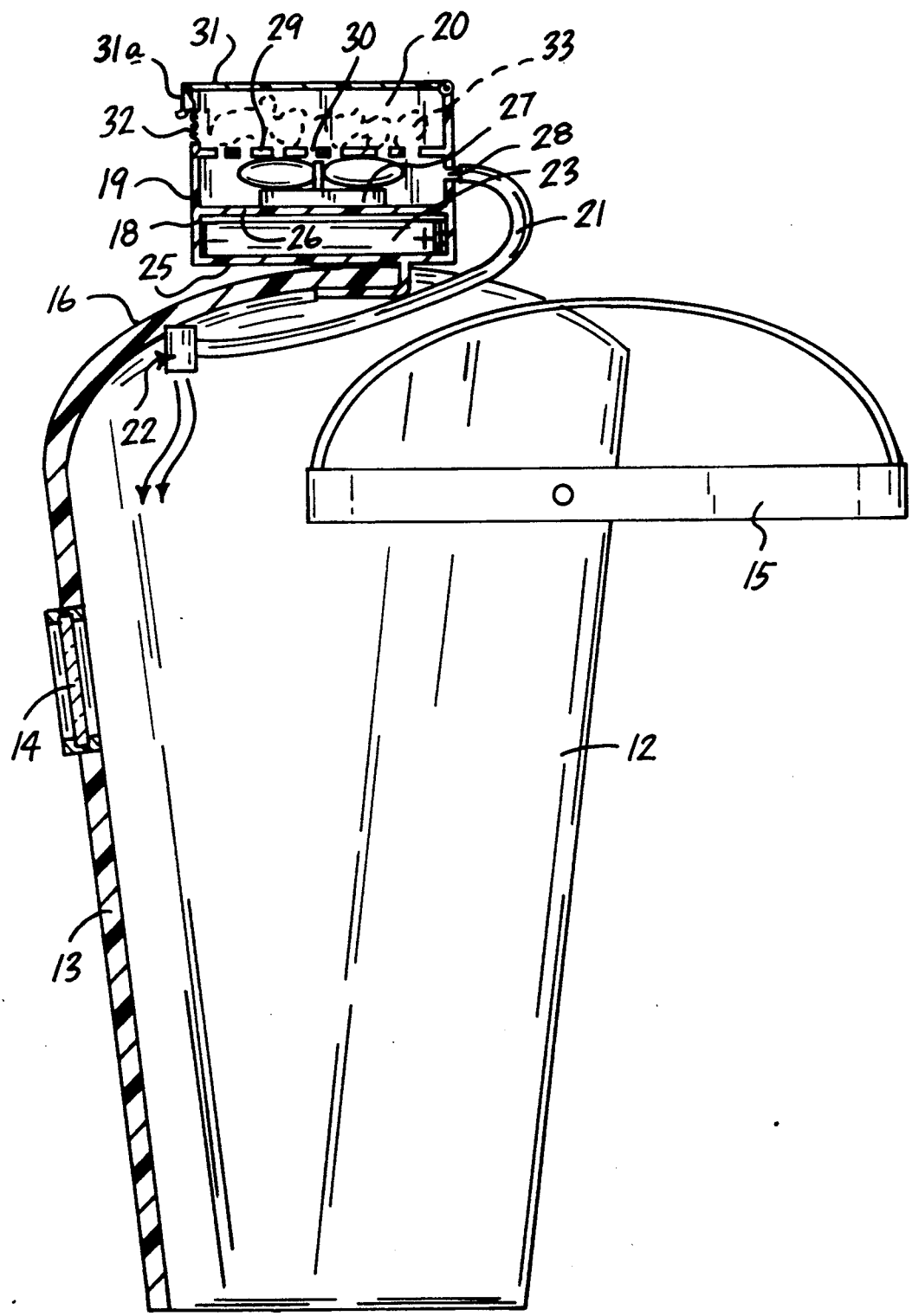
FIG. 4 is an orthographic view, taken along the lines 4—4 of FIG. 3 in the direction indicated by the arrows.

A housing member 17 is mounted to the top wall 16 in an integral secured relationship, With the housing member 17 including a housing first lower chamber 18, a housing second medial chamber 19, and a housing third top chamber 20 (see FIG. 4). The medial second chamber 19 includes an air flow conduit 21 directed thereto to a nozzle 28 mounted to a rear wall of the medial chamber 19, with the air flow conduit 21 directed downwardly and secured to an air flow manifold 22 mounted to an interior surface of the top wall below the housing member 17.

The first lower chamber 18 includes at least one battery or a plurality of batteries 23 operative through an on/off switch 24 mounted to a side wall of the housing member 17 of the first lower chamber 18. A first chamber floor 15 is mounted to the top wall 16 of the helmet member 11. The first chamber 18 includes a first chamber roof 26. To a top surface of the first chamber roof 26 is mounted a blower fan member 27 in electrical communication with the batteries 23 and switch 24 to effect selective actuation of the blower fan member 27 through utilization of the switch 24. The blower fan member 27 underlies a second chamber roof 29 of the second chamber 19, with the second chamber 29 including a matrix of apertures 30 directed therethrough to direct air flow through the first chamber 18, through the second chamber 19, and into the air flow conduit 21. The third top chamber 20 includes a third chamber lid 31 hingedly mounted to a rear wall of the third chamber, with a forward flange of the third chamber lid including a clasp 31a to secure the third chamber lid 31 to a forward wall of the third chamber. The third chamber further includes an air inlet screen 32 directed through the forward wall of the third chamber below the clasp 31a to direct air flow into the third chamber. A cooling medium 33, such as frozen carbon dioxide known as "dry ice", is positioned within the third chamber, whereupon air flow through the third chamber and subsequently through the conduit 21 and manifold 22 directs a cooling flow of air along an interior surface of the forward wall 13, as indicated by the arrows in FIG. 4.

FIG. 6 illustrates the air flow manifold 22, with the manifold rear wall 34 receiving the air flow conduit 21, with the manifold bottom wall 35 including a series of bottom wall apertures 36. The manifold further includes a single or plurality of aperture plugs 37 formed of a conical configuration, with an aperture plug 37 receivable selectively within one or a plurality of the bottom wall apertures 36 to control air flow through the manifold along the interior surface of the forward wall 13. In this manner, metered flow of the cooled air is available, whereas the manifold is of a longitudinal configuration extending generally coextensively with the forward wall above the window 14, whereupon selective plugging of the apertures 36 directs not only the quantity of air, but the direction of air relative to the interior surface of the forward wall 13.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A ventilated welding mask apparatus, comprising,
a unitary helmet member, the helmet member including spaced side walls, a forward wall, and a viewing window, the forward wall including a forward wall exterior surface and a forward wall interior surface, and the viewing window extending through the forward wall, and
a securement strap member mounted to the side walls, and
the top wall including a housing member, the housing member including air flow means, and
an air flow conduit directed to the housing member, and
the air flow means arranged for directing air flow through the air flow conduit, and
an air flow manifold, and
a lower terminal end of the air flow conduit directed to the air flow manifold, and
the air flow manifold including a plurality of apertures to direct air flow from the air flow conduit through the air flow manifold, and the air flow manifold fixedly mounted to the interior surface of the top wall spaced above and parallel the viewing window, with the air flow manifold directed substantially coextensive with the interior surface of the top wall, and
the air flow means is mounted within the housing member, and the air flow means includes a first lower chamber mounted within the housing member, and a second medial chamber positioned above the first lower chamber within the housing member, and a third top chamber mounted within the housing member above the second medial chamber, and the second medial chamber includes a second medial chamber rear wall, and a nozzle mounted to the second medial chamber rear wall, wherein the air flow conduit is secured to the nozzle remote from the air flow manifold.

2. An apparatus as set forth in claim 1 wherein the first lower chamber includes a first lower chamber floor and a first lower chamber side wall, with the first lower chamber side wall including a switch member, and at least one battery mounted within the first lower chamber, and the first lower chamber including a first lower chamber roof, and a blower fan motor mounted within the second medial chamber on the first lower chamber roof, and the switch operative to direct electrical energy to the lower frame member for selective actuation of the blower fan member.

3. An apparatus as set forth in claim 2 wherein the second medial chamber includes a second medial chamber roof, and the second medial chamber roof includes a matrix of apertures directed therethrough, and the third top chamber includes a third chamber lid, the third chamber lid hingedly mounted to the third chamber, and the third chamber lid including a clasp mounted to a forward edge of the third chamber lid, and the third chamber further including a third chamber forward wall, and the clasp securably and removably mounted relative to the third chamber forward wall, and the third chamber forward wall further including an inlet screen coextensive with the third chamber forward wall.

4. An apparatus as set forth in claim 3 wherein a cooling medium is mounted within the third top chamber, wherein the third chamber lid permits selective replenishment of the cooling medium.

5. An apparatus as set forth in claim 4 wherein the cooling medium includes carbon dioxide.

6. An apparatus as set forth in claim 5 wherein the manifold includes a manifold rear wall, the manifold rear wall has secured thereto the lower terminal end of the air flow conduit, and the manifold further including a manifold bottom wall, the manifold bottom wall including a series of equally spaced bottom wall apertures directed therethrough.

7. An apparatus as set forth in claim 6 wherein at least one conical plug member is provided, and the conical plug member is removably mounted within at least one of said bottom wall apertures to permit selective metering of air flow through the bottom wall apertures.

* * * * *